United States Patent
McCormick et al.

(10) Patent No.: US 8,177,064 B2
(45) Date of Patent: May 15, 2012

(54) SURGICAL PACK AND TRAY

(75) Inventors: Matthew McCormick, Forest Falls, CA (US); Lawrence Chong, Seal Beach, CA (US); Ralph Kerns, Laguna Niguel, CA (US); Charles DeBoer, Pasadena, CA (US); Mark Humayun, Glendale, CA (US)

(73) Assignee: Doheny Eye Institute, Los Angeles, CA (US)

( * ) Notice: Subject to any disclaimer, the term of this patent is extended or adjusted under 35 U.S.C. 154(b) by 267 days.

(21) Appl. No.: 12/106,962

(22) Filed: Apr. 21, 2008

(65) Prior Publication Data

US 2008/0272023 A1 Nov. 6, 2008

Related U.S. Application Data

(60) Provisional application No. 60/925,548, filed on Apr. 20, 2007.

(51) Int. Cl.
*B65D 83/10* (2006.01)
(52) U.S. Cl. ........................................ 206/370; 206/564
(58) Field of Classification Search .................. 206/369, 206/370, 557, 564, 565, 561, 63.5
See application file for complete search history.

(56) References Cited

U.S. PATENT DOCUMENTS

| | | | |
|---|---|---|---|
| 3,116,828 A * | 1/1964 | Glassman | 206/564 |
| 3,293,430 A * | 12/1966 | Wustner | 378/174 |
| 3,702,940 A | 11/1972 | Stewart | |
| 3,820,656 A * | 6/1974 | Orr | 206/570 |
| 3,976,195 A * | 8/1976 | Cohen | 206/362 |
| 3,986,263 A | 10/1976 | Borgelt et al. | |
| 4,011,944 A * | 3/1977 | Cooley et al. | 206/557 |
| 4,014,342 A | 3/1977 | Staub et al. | |
| 4,108,182 A | 8/1978 | Hartman et al. | |
| 4,266,669 A * | 5/1981 | Watson | 206/564 |
| 4,288,733 A | 9/1981 | Bilanceri et al. | |
| 4,293,074 A | 10/1981 | Dunsky | |
| 4,320,761 A | 3/1982 | Haddad | |
| 4,378,108 A | 3/1983 | Bailey, Jr. | |
| 4,428,748 A | 1/1984 | Peyman et al. | |
| 4,430,062 A | 2/1984 | Henrichsen et al. | |
| 4,869,266 A | 9/1989 | Taylor et al. | |

(Continued)

FOREIGN PATENT DOCUMENTS

JP 2005-046412 2/2005

(Continued)

OTHER PUBLICATIONS

International Search Report and Written Opinion. PCT/US2008/061058. Dated Aug. 27, 2008.

(Continued)

*Primary Examiner* — Jacob K Ackun
(74) *Attorney, Agent, or Firm* — Knobbe, Martens, Olson & Bear, LLP

(57) ABSTRACT

A surgical pack includes a platform having a plurality of recesses configured to function as a surgical tray. A plurality of surgical instruments are contained in a corresponding recess of the platform. The recess may have the shape of the surgical instrument that it is designed to receive. The recess may also include safety mechanisms to protect the tips of certain instruments and to lower the risk of injury caused by them. A packaging or covering holds the platform and the plurality of surgical instruments in a substantially sterile condition.

51 Claims, 6 Drawing Sheets

U.S. PATENT DOCUMENTS

| | | | |
|---|---|---|---|
| 4,889,231 A * | 12/1989 | Foote et al. | 206/363 |
| 4,974,728 A | 12/1990 | Colton | |
| 5,392,917 A * | 2/1995 | Alpern et al. | 206/570 |
| 5,399,007 A | 3/1995 | Marconet | |
| 5,455,766 A | 10/1995 | Scheller et al. | |
| 5,508,836 A | 4/1996 | DeCaro et al. | |
| 5,627,584 A | 5/1997 | Nishikori et al. | |
| 5,746,719 A | 5/1998 | Farra et al. | |
| 5,779,053 A * | 7/1998 | Partika et al. | 206/570 |
| 5,873,717 A | 2/1999 | Behringer | |
| 6,024,699 A | 2/2000 | Surwit et al. | |
| 6,051,011 A | 4/2000 | Weidenbenner | |
| 6,059,795 A | 5/2000 | Wallace et al. | |
| 6,074,399 A | 6/2000 | Wallace et al. | |
| 6,117,127 A | 9/2000 | Helmreich et al. | |
| 6,158,437 A | 12/2000 | Vagley | |
| 6,185,096 B1 | 2/2001 | Helot et al. | |
| 6,251,113 B1 | 6/2001 | Appelbaum et al. | |
| 6,258,111 B1 | 7/2001 | Ross et al. | |
| 6,312,258 B1 * | 11/2001 | Ashman | 433/172 |
| 6,355,047 B1 | 3/2002 | Wallace et al. | |
| 6,428,487 B1 | 8/2002 | Burdorff et al. | |
| 6,616,606 B1 | 9/2003 | Petersen et al. | |
| 6,641,039 B2 | 11/2003 | Southard | |
| 6,648,223 B2 | 11/2003 | Boukhny et al. | |
| 6,666,875 B1 | 12/2003 | Sakurai et al. | |
| 6,716,219 B1 | 4/2004 | Koch | |
| 6,896,141 B2 * | 5/2005 | McMichael et al. | 206/571 |
| 7,114,500 B2 | 10/2006 | Bonutti | |
| 7,267,246 B2 * | 9/2007 | Eiskant et al. | 220/782 |
| 7,401,703 B2 * | 7/2008 | McMichael et al. | 206/570 |
| 7,431,157 B2 * | 10/2008 | Porret et al. | 206/439 |
| 7,604,007 B1 | 10/2009 | Wooley | |
| 2001/0022615 A1 | 9/2001 | Fernandez et al. | |
| 2002/0013517 A1 | 1/2002 | West et al. | |
| 2003/0093503 A1 | 5/2003 | Yamaki et al. | |
| 2003/0165794 A1 | 9/2003 | Matoba | |
| 2004/0004019 A1 * | 1/2004 | Busch | 206/571 |
| 2004/0116952 A1 | 6/2004 | Sakurai et al. | |
| 2004/0138518 A1 | 7/2004 | Rise et al. | |
| 2004/0186683 A1 | 9/2004 | Farber et al. | |
| 2004/0208780 A1 | 10/2004 | Faries, Jr. et al. | |
| 2004/0243147 A1 | 12/2004 | Lipow | |
| 2005/0128987 A1 | 6/2005 | Liang | |
| 2005/0283138 A1 | 12/2005 | Tashiro et al. | |
| 2006/0002258 A1 | 1/2006 | Nakamura et al. | |
| 2006/0046226 A1 | 3/2006 | Bergler et al. | |
| 2006/0086634 A1 | 4/2006 | Steppe | |
| 2006/0100497 A1 | 5/2006 | Sawazaki et al. | |
| 2006/0109105 A1 | 5/2006 | Varner et al. | |
| 2006/0119481 A1 | 6/2006 | Tethrake et al. | |
| 2006/0142739 A1 | 6/2006 | DiSilestro et al. | |
| 2006/0244593 A1 | 11/2006 | Nycz et al. | |
| 2006/0272979 A1 | 12/2006 | Lubbers et al. | |
| 2007/0290654 A1 | 12/2007 | Govari et al. | |
| 2008/0030345 A1 | 2/2008 | Austin et al. | |
| 2008/0041282 A1 * | 2/2008 | Goschy et al. | 108/141 |
| 2008/0120137 A1 | 5/2008 | Nyholm | |
| 2008/0281254 A1 | 11/2008 | Humayun et al. | |
| 2008/0281301 A1 | 11/2008 | DeBoer et al. | |
| 2009/0143734 A1 | 6/2009 | Humayun et al. | |
| 2010/0174415 A1 | 7/2010 | Humayun et al. | |
| 2011/0190690 A1 | 8/2011 | Humayun et al. | |

FOREIGN PATENT DOCUMENTS

| | | |
|---|---|---|
| WO | WO 99/66444 | 12/1999 |
| WO | WO 00/32115 | 6/2000 |
| WO | WO00/32123 | 6/2000 |
| WO | WO 03/034213 A2 | 4/2003 |

OTHER PUBLICATIONS

International Search Report and Written Opinion. PCT/US2008/061043. Dated Sep. 2, 2008.

U.S. Appl. No. 12/107,038, including its prosecution history, and the Office Actions therein, Humayun, Mark, et al.

U.S. Appl. No. 12/107.052, including its prosecution history, and the Office Actions therein, DeBoer, Charles, et al.

U.S. Appl. No. 12/256,420, including its prosecution history, and the Office Actions therein, Humayun, Mark, et al.

International Search Report and Written Opinion Received in PCT/US08/061065 Dated Dec. 22, 2008.

Partial International Search Report in Application No. PCT/US2008/080832 mailed on Apr. 27, 2010.

U.S. Appl. No. 12/684,850, including its prosecution history, and the Office Actions therein, Humayun, Mark, et al.

International Search Report and Written Opinion in Application No. PCT/US2008/080832 mailed on Jul. 29, 2010.

U.S. Appl. No. 13/084,478, including its prosecution history, and the references cited and the Office Actions therein. Not Yet Published, DeBoer, et al.

Extended European Search Report received in European Application No. 08746468.1, dated Nov. 23, 2010.

International Preliminary Report on Patentability and Written Opinion mailed on Oct. 29, 2009 in PCT Application No. PCT/US2008/061058 filed Apr. 21, 2008.

International Preliminary Report on Patentability and Written Opinion mailed on Apr. 26, 2011 in PCT Application No. PCT/US2008/080832 filed Oct. 22, 2008.

International Search Report and Written Opinion mailed on Jun. 2, 2011 in PCT Application No. PCT/US2011/020415 filed Jan. 6, 2011.

* cited by examiner

SURGICAL PACK AND TRAY

CROSS-REFERENCE TO RELATED APPLICATION(S)

This application claims the benefit of U.S. Provisional Application No. 60/925,548, filed on Apr. 20, 2007, the content of which is incorporated herein by reference. This application is also related to U.S. application Ser. No. 12/107,052, entitled "Personal Surgical Center," and U.S. application Ser. No. 12/107,038, entitled "Independent Surgical Center," both filed on Apr. 21, 2008, the content of both of which are incorporated herein by reference.

FIELD OF THE INVENTION

The present invention relates to surgical packs (or packages). In particular, it relates to surgical packs that are configured to provide tray-like features.

BACKGROUND

Existing surgical packs provide sterile storage environments for surgical components (instruments, drugs, solutions, and the like) that are required for a surgical procedure, such as an ophthalmic procedure. One known example of a surgical pack is the Custom-Pak®, which is available from Alcon, Inc. Upon opening of this surgical pack, components may be retrieved according to a particular sequence by which they are required during a procedure.

Often times, after the pack is opened, the components within the pack are retrieved and transferred to a conventional mayo tray, as is known in the art, or back table in an operating room such that a surgeon can retrieve and, if he/she desires, place back any of the components during an operation. The surgical pack does not provide the surgeon with rapid access to all of the packaged components upon opening of the pack. Rather, the transfer of the components to a mayo tray or back table is generally required for the rapid access. Often times, a scrub nurse or surgical assistant performs this transfer. Furthermore, current surgical packs do not provide the surgeon with the ability to return components to the pack such that they are secured positioned but removable for later retrieval during the operation.

Existing surgical packs also do not include all of the components that a surgeon would need for a surgery. For example, although the pack may include the necessary cutting tips, they do not include the handpieces to which the cutting tips are connected. Furthermore, existing surgical packs do not include a prefilled infusion and aspiration cassette.

Another known example of a surgical pack is the 25-Gauge High-Speed Vitrectomy Pack, which is available from Bausch and Lomb, Inc. Use of the Vitrectomy Pack, however, raises issues similar to those described above in reference to the Custom-Pak®. That is, after the pack is opened, packaged components are retrieved and transferred to a mayo or back table for retrieval and use by a surgeon due to the lack in existing packs to allow components to be securely placed back after retrieval while at the same time providing easy accessibility to the placed-back components for later use.

As such, there is a need for a surgical pack that provides rapid access to packaged components without transfer of the components to a separate tray or table. There is also a need for a surgical pack that is configured for secure re-storage and retrieval of components.

SUMMARY OF THE INVENTION

One aspect of embodiments of the present invention is directed to a surgical pack that provides rapid access to packaged components without requiring the transfer of the components to a separate tray or table. Another aspect of embodiments of the present invention is directed to a surgical pack that is configured to provide secure re-storage of the retrieved instrumentation when not in use.

According to one embodiment, the present invention is directed to a surgical apparatus that includes a platform having a plurality of recesses located on a first side of the platform. The first side of the platform has a substantially sterile surface. The surgical apparatus also includes a plurality of surgical instruments, each of the surgical instruments being removably positioned in a corresponding one of the recesses. A cover is removably affixed to the platform at the first side of the platform for covering at least the first side of the platform and the surgical instruments. The cover is adapted to preserve the sterility of the first side at least until the cover is removed.

The platform is configured to sit on a surgical stand to the side of or on top of the patient. According to one embodiment of the invention, the platform has two ends extending substantially along a first direction and spaced apart from each other along a second direction that is substantially perpendicular to the first direction for accommodating a head of a patient or another body part between the two ends.

According to one embodiment of the invention, the platform is substantially U-shaped or has any other geometric shape configured to accommodate the body part. According to one embodiment, the platform surrounds the periphery of the patient's head. The platform may include an attachment location at which a surgical drape may be removably attached, and/or include armrests or arm rest locations for use by the surgeon.

According to one embodiment of the invention, at least one of the surgical instruments has a substantially sharp end, and the one of the recesses corresponding to the at least one of the surgical instruments comprises a covering for substantially shielding the substantially sharp end. The portion of the recesses corresponding to the sharp end may also be configured to substantially conform to the shape of the sharp end. Furthermore, the recess holding the at least one of the surgical instruments may have a depth configured to contain the substantially sharp end deeper in the recess than a handle portion of the instrument. All these mechanisms help prevent the sharp end from damage, as well as helping lower the risk of injury to a user of the instruments.

According to one embodiment of the invention, the platform has identifiers located in relation to the recesses. The identifiers correspond to the surgical instruments positioned in the recesses and may take the form of tactile identifiers, light emitting diode (LED) display, colored code, or the like.

According to one embodiment of the invention, the platform accommodates a substantially sterile barrier accessible by a substantially non-sterile user wearing substantially sterile protection for providing assistance during a surgical procedure.

According to another embodiment, the present invention is directed to a surgical pack that includes a platform having a plurality of recesses configured to function as a surgical tray. The surgical pack also includes a plurality of surgical instruments. Each of the surgical instruments are removably positioned in a corresponding one of the recesses. The corresponding one of the recesses has a shape that substantially confirms to the shape of the surgical instrument being received. A packaging holds the platform and the plurality of surgical instruments in a substantially sterile condition.

According to another embodiment, the present invention is directed to a method for providing instrumentation during a surgical procedure. The method includes providing a surgical pack as described above. The method further includes removing the platform with the plurality of surgical instruments positioned in the corresponding recesses from the packaging, placing the platform in close proximity to a surgeon and a patient, removing at least one of the surgical instruments from the corresponding recess for a first part of the surgical procedure, and returning the at least one of the surgical instruments to the corresponding recess after the first part of the surgical procedure. The platform may be easily disposed of at the conclusion of the procedure. For example, the platform may be placed in a separate container and sent back to a factory for recycling, refurbishment, or disposal.

According to one embodiment of the invention, the surgical pack includes substantially all or most of the components required for a surgery or procedure integrated into the pack. The components may include, for example, a biological tissue cutter, tissues illuminator, fluid/air infusion and aspiration cassette, syringes for gas exchange, a small sterile package of balanced salt solution (BSS) for priming the cutter, disposable forceps, Q-tips, and the like. Aspiration/irrigation capabilities may also be integrated into the tray.

BRIEF DESCRIPTION OF THE DRAWINGS

The above and other embodiments of the present invention will be appreciated as the same become better understood with reference to the specification, claims and appended drawings wherein:

DETAILED DESCRIPTION

The detailed description set forth below in connection with the appended drawings is intended as a description of exemplary embodiments of surgical packs provided in accordance with the present invention and is not intended to represent the only forms in which the present invention may be constructed or utilized. The description sets forth the features of the surgical packs of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features. Furthermore, the terms surgical pack and surgical tray are used interchangeably as the surgical pack functions as the tray once the packaging is removed.

In general terms, embodiments of the present invention are directed to a surgical pack configured for rapid access to packaged components without requiring the transfer of the components to a separate tray or table. In this regard, the surgical pack, upon opening, serves as a sterile tray for a surgical procedure. The surgical pack contains the instrumentations ready for use, already setup on the pack/tray. The instrumentations are positioned at suitably convenient locations from which the surgeon can remove, use, and put back the instrumentation when not in use. The surgical pack also includes accommodations for instruments having sharp ends to protect the sharp ends when the instruments are stored and not in use. The accommodations may include, for example, a protective cover adjacent to the sharp ends. At least some of the sharp ends are positioned to face away from the surgeon.

Figure 1A:
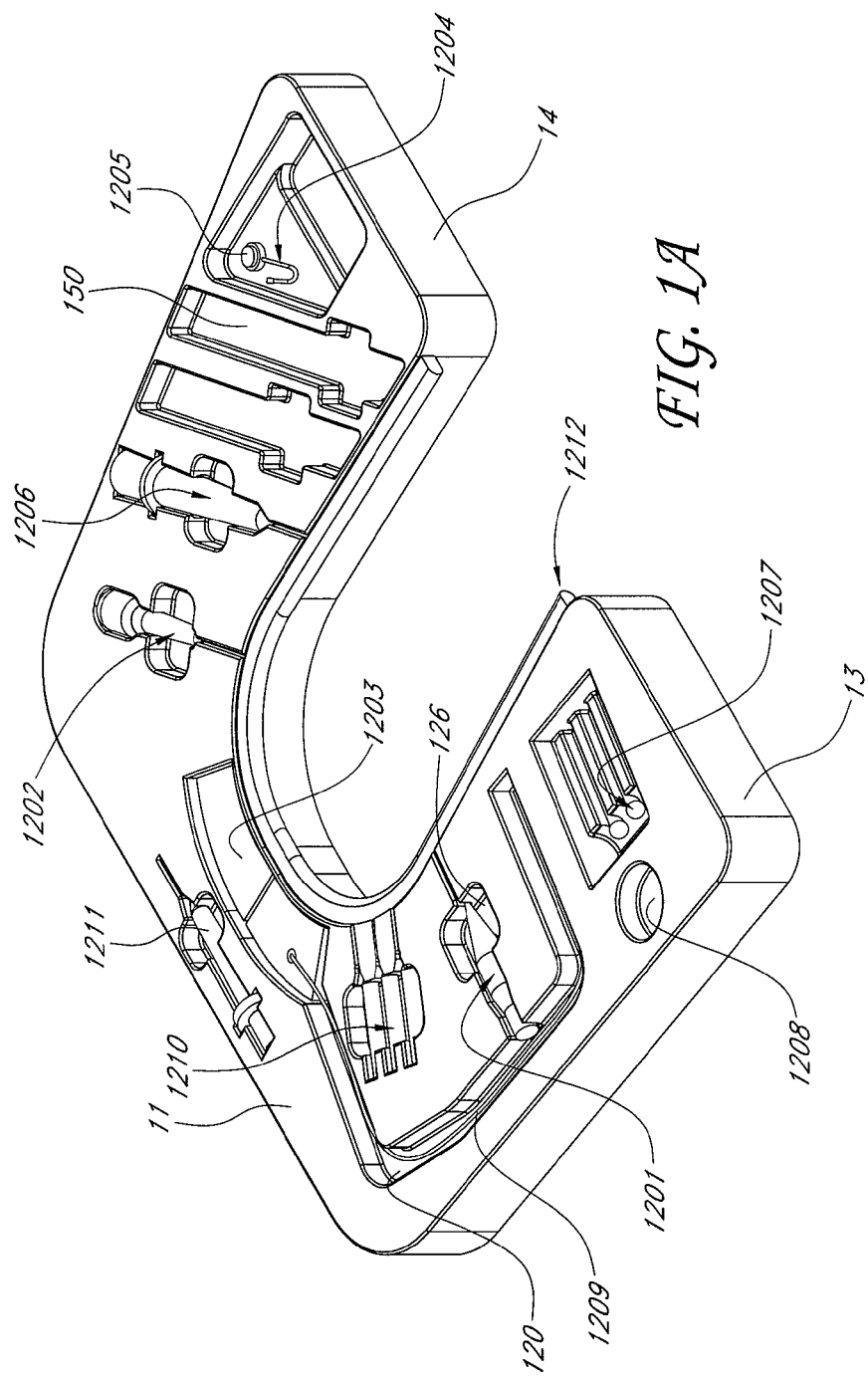
FIG. 1A illustrates a top perspective view of a surgical pack according to an embodiment of the present invention.
Figure 1B:
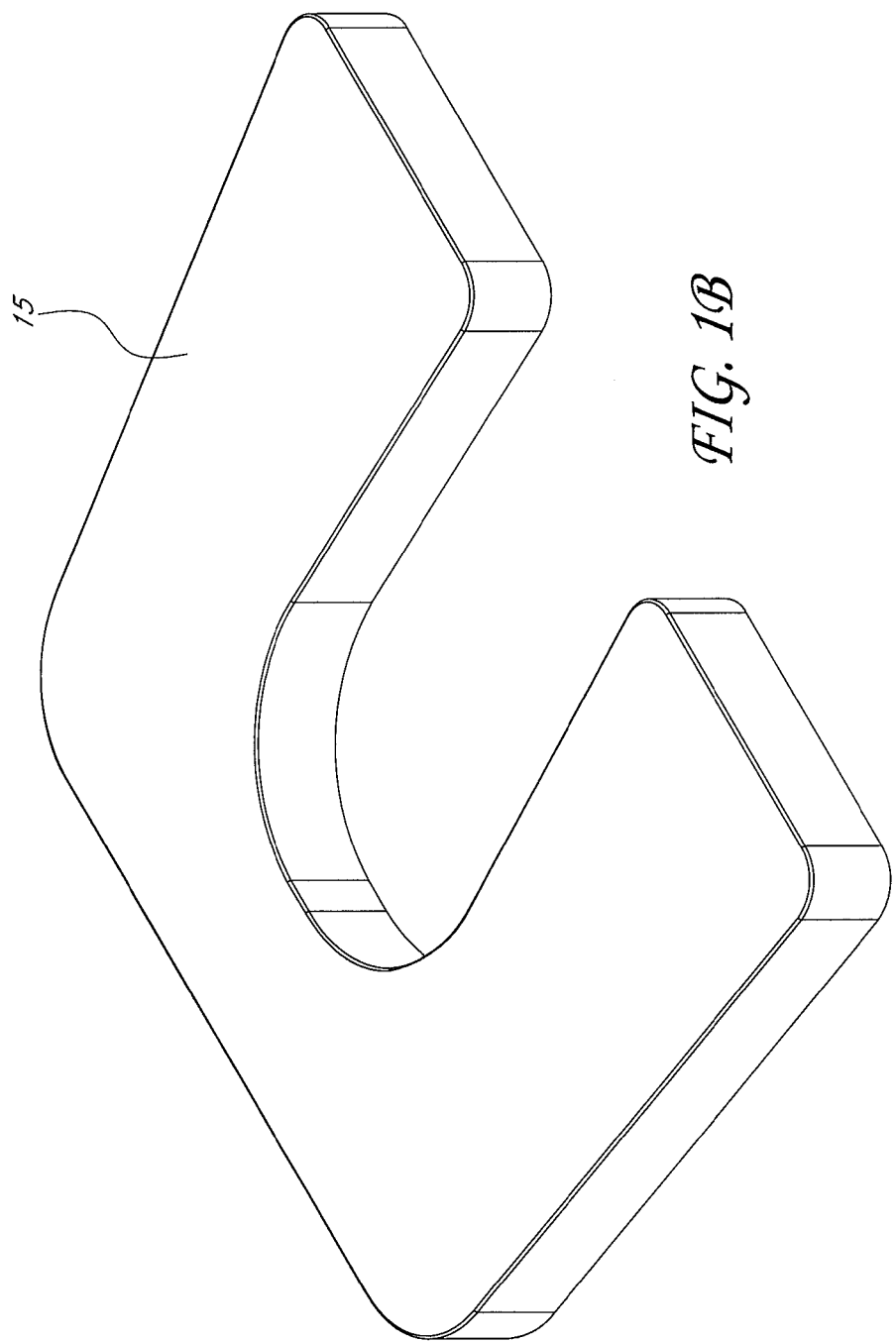
FIG. 1B illustrates a top perspective view of a covering for the surgical pack according to one embodiment of the present invention.
Figure 1C:
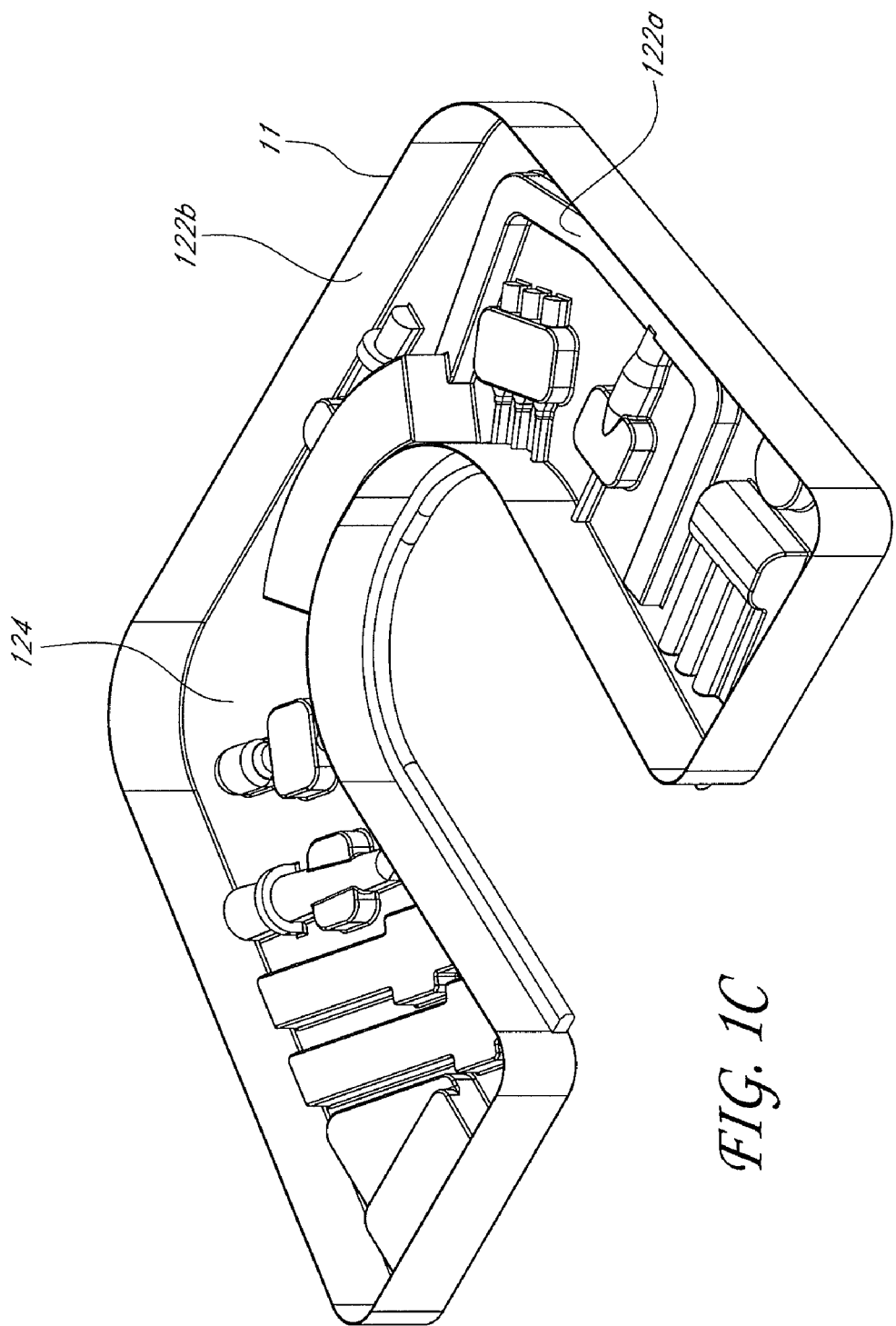
FIG. 1C illustrates a bottom perspective view of a surgical pack according to an embodiment of the present invention.

With reference to FIGS. 1A-1C, according to one embodiment of the present invention, a surgical pack includes a tray (also referred to as a platform) 11 having multiple recesses (for example, recess 120) located on an upwardly facing side of the tray 11. The recesses translate into corresponding protrusions such as, for example, protrusions 122a, 112b on an underside 124 of the tray (FIG. 1C). According to one embodiment of the invention, the tray is made of a material designed to be thin and lightweight, such as, for example, plastic. A person of skill in the art should recognize, however, the other materials other than plastic which are conventional in the art may also be used.

According to an alternate embodiment of the invention, in addition or in lieu of the recesses, the tray may include multiple pockets for containing one or more instruments. In yet other alternate embodiments, cradles that can be repositioned to aid in retrieval of surgical devices Surgical components are positioned at all or fewer than all of the recesses. For example, in one exemplary embodiment, surgical components of the surgical pack include: a biological tissue cutter 1201; a tissue illuminator 1202; an aspiration/infusion cassette 1203; a disposable speculum/drape combination 1204; a self stabilizing lens ring 1205 with the lens pre-mounted; a gas exchange syringe 1206; Q-tips 1207; a sterile container 1208 containing balanced salt solution (BSS); an infusion line 1209; trocars 1210 with cannulas pre-mounted; and goniosol 1211.

Embodiments of the present invention are not limited to the above components and may include other instrumentation such as: a drape which a patient's head may be covered; a device for air/fluid exchange; a syringe for oil exchange; a syringe for Triameinolone steroid; a sterile barrier; and/or disposable forceps. One skilled in the art will appreciate that the surgical pack may include any combination of the above components and the like.

According to one embodiment of the invention, the aspiration/infusion cassette 1203 is mounted directly into the tray. This eliminates the need for separate setup of the aspiration/infusion cassette. An aspiration line connects the biological tissue cutter 1201 to the aspiration chamber of the cassette for removing tissue cut or dislodged by the cutter during surgery. The infusion line 1209 connects the infusion chamber of the cassette and allows infusion of fluids such as, for example, the balanced salt solution, to replace the aspirated materials.

The tray also includes an attachment mechanism, such as, for example, ridge 1212, for attaching the speculum and drape combination 1204 during surgery. A drape may also be positioned under the patient's head and/or underside of the tray to trap or catch any fluids.

According to one embodiment of the invention, the tray includes one or more mechanisms for latching of the tray onto a surgeon's chair, a surgical platform, or a separate stand. The latching mechanism may include, for example, a snap fit onto the support bar or any other mechanism conventional in the art for preventing or resisting movement of the tray.

The tray may also include portions where instrumentation is not stored to provide armrests or rest locations for the surgeon's arms.

According to one embodiment of the invention, any instruments having sharp ends (e.g. needles, blades, etc.) are configured to be covered such that their sharp ends are not accessible from the armrests or rest locations. In addition, the tray includes unoccupied recesses (see, for example, recess 150). Such unoccupied recesses provide storage locations for other instruments that are not included in the surgical pack but may be used during an operation. Examples of other instruments may include a phacoemulsification handpiece, forceps, laser probe, scissors, or the like. During the operation, the surgeon may place such instruments in the unoccupied recesses.

According to one embodiment of the invention, the tray may also be configured with a processing unit (e.g. a microprocessor, ASIC, and/or circuitry and drive mechanism) and internal power configured to control and provide power to various instrumentations that require power and control as is described in further detail in U.S. application Ser. No. 12/107,038, entitled "Independent Surgical Center," filed on Apr. 21, 2008. For example, the processing unit may be configured to power and control the cutter 201. The tray may further be equipped for wireless communication with one or more other instrumentations. For example, the tray may wirelessly communicate with the illuminator 1202 for receiving current operating parameters, such as, for example, a current illumination level. In this manner, all the necessary logic, circuitry, and power resides within the tray itself and/or instruments in communication with the tray without having to resort to a separate control console.

According to one embodiment of the invention, at least the upwardly facing side of the tray 11 is configured to be sterile. A covering 15 (FIG. 1B) is positioned over at least the upwardly facing side of the tray 11 to preserve the sterility of the tray. A person of skill in the art should recognize that the covering 15 may take any form that is conventional in the art. For example, the covering 15 may be a plastic film that is adhered to the upwardly facing circumference of the tray. Alternatively, the covering 15 may be a plastic bag that contains the entire tray until it is removed from the bag for a procedure. In yet another embodiment, the covering 15 may be affixed to the tray via hinges that allow the tray to be opened during use, and closed after a procedure. Alternatively, the covering may be a plastic top shaped in the shape of the tray (FIG. 1B) which snaps into place on top of the tray and is further secured, foe example, via adhesives.

FIG. 1C shows a bottom perspective view of the tray 11 according to an embodiment of the present invention. As depicted here, the underside of the tray is hollow with various protrusions, such as, for example, protrusions 122a, 112b, that correspond to the recesses on the upwardly facing side of the tray.

According to one embodiment, the tray 11, itself is a component of the packaging of the instrumentation. The use of the tray as the surgical pack itself avoids the need for a separate mayo tray or back table for setting the instrumentation contained in the pack. Furthermore, the various instrumentations commonly contained in the surgical pack are pre-arranged in their appropriate locations within the tray. As such, setup time that would normally be incurred to position the instrumentation at the beginning of a particular procedure is no longer required.

During an operation, after the pack is opened by removing the covering 15 or removing the tray from an enclosure, the tray 11 may be placed at the left or right side of the surgeon, on the patient's chest, or on another surgical apparatus such as a surgical stand in close proximity to the surgeon and the patient. According to one embodiment of the invention, the tray is positioned between the surgeon and the head of the patient.

Instruments are located in the tray to provide the surgeon access to all instrumentation. For example, instrumentation that is commonly retrieved more than once during a procedure (e.g., illuminator, cutter, etc.) may conveniently be located at a portion of the tray that is arranged closest or closer to the surgeon. In contrast, instrumentation that is retrieved less often during a procedure (e.g., instrumentation such as Q-tips and lens ring, which are generally retrieved only once) may be located at a portion of the tray that is arranged furthest or further from the surgeon.

According to one embodiment of the invention, each component has a specific location in the tray, and after it is used, is securely put back in the tray. According to one embodiment, each recess has a shape generally conforming to the shape of the specific component which it is configured to receive. Thus, when the component is returned to the corresponding recess on the tray, the conforming shape of the recess allows the component to be snugly held in place. According to one embodiment of the invention, the recess is generally in the shape of the recess that it is configured to receive except for additional portions 126 of the recess that are configured to receive the fingers of the surgeon for facilitating manual retrieval of the component.

In one embodiment, the positions of the instrumentation on the tray 11 are labeled such that they may be easily located. For example, the positions may be labeled using a Braille system or other tactile mechanism, a color coding system, or LED illumination. As such, a surgeon may not require the assistance of a scrub nurse to handle the surgeon instrumentation during the procedure. This and other described features of embodiments of the present invention are particularly useful where surgical procedures are conducted in environments away from the conventional operating room, e.g., in a surgeon's own office. According to one embodiment of the invention, the independent surgical center and/or instruments are contained in procedure specific surgical packs. For example, an exemplary surgical pack may contain a biological tissue cutting and fluid aspiration system, a biological tissue illuminator, an aspiration and infusion cassette, and other disposable instrumentation. Such other disposable instrumentation may include a disposable speculum/drape combination, syringe for local anesthesia, air/fluid exchange device, syringe for oil exchange, syringe for Triamcinolone steroid, disposable forceps, q-tips, beta-iodine for sterilization, small sterile container with balanced salt solution (BSS), and trocars with pre-mounted cannulas. The surgical packs may be adaptable and customizable for specific surgeons. Furthermore, the instrument holders within the surgical pack may be illuminated via LEDs and the like for identifying the instruments held by the pack. In general terms, embodiments of the present invention are directed to a surgical pack configured for rapid access to packaged components without requiring the transfer of the components to a separate tray or table. In this regard, the surgical pack, upon opening, serves as a sterile tray for a surgical procedure. The surgical pack contains the instrumentations ready for use, already setup on the pack/tray.

In an embodiment of the present invention, for convenience and safety benefits, the handles (or handpieces) of all instrumentation, including syringes and Q-tips, remain uncovered during use and are positioned for easy surgeon retrieval. In contrast, at least some sharp ends of the instrumentation such as trocars and needles are positioned in the tray and are configured to be covered when not in use. In this regard, the recesses corresponding to instrumentation having sharp ends may be configured to have a depth such that the sharp ends do not outwardly protrude from the tray when such instrumentation is stored on the tray. For example, these recesses may gradually increase in depth from an end which receives the handle of the instrumentation to another end which receives the sharp end of the instrumentation.

In another embodiment of the present invention, other safety features are employed to lower the risk of injury caused by sharp ends of certain instruments. For example, portions of recesses where sharp ends of certain instruments are stored may have a cover/shield over the sharp ends. The cover or shield may be integrated on the tray. For example, the cover may be a roof that is raised in the shape of a dome or lay flat across the portion of the recess housing the sharp ends. In another example, the recesses may be configured and sized to provide a more snug or close fit with the sharp ends of stored instruments.

Figure 2:
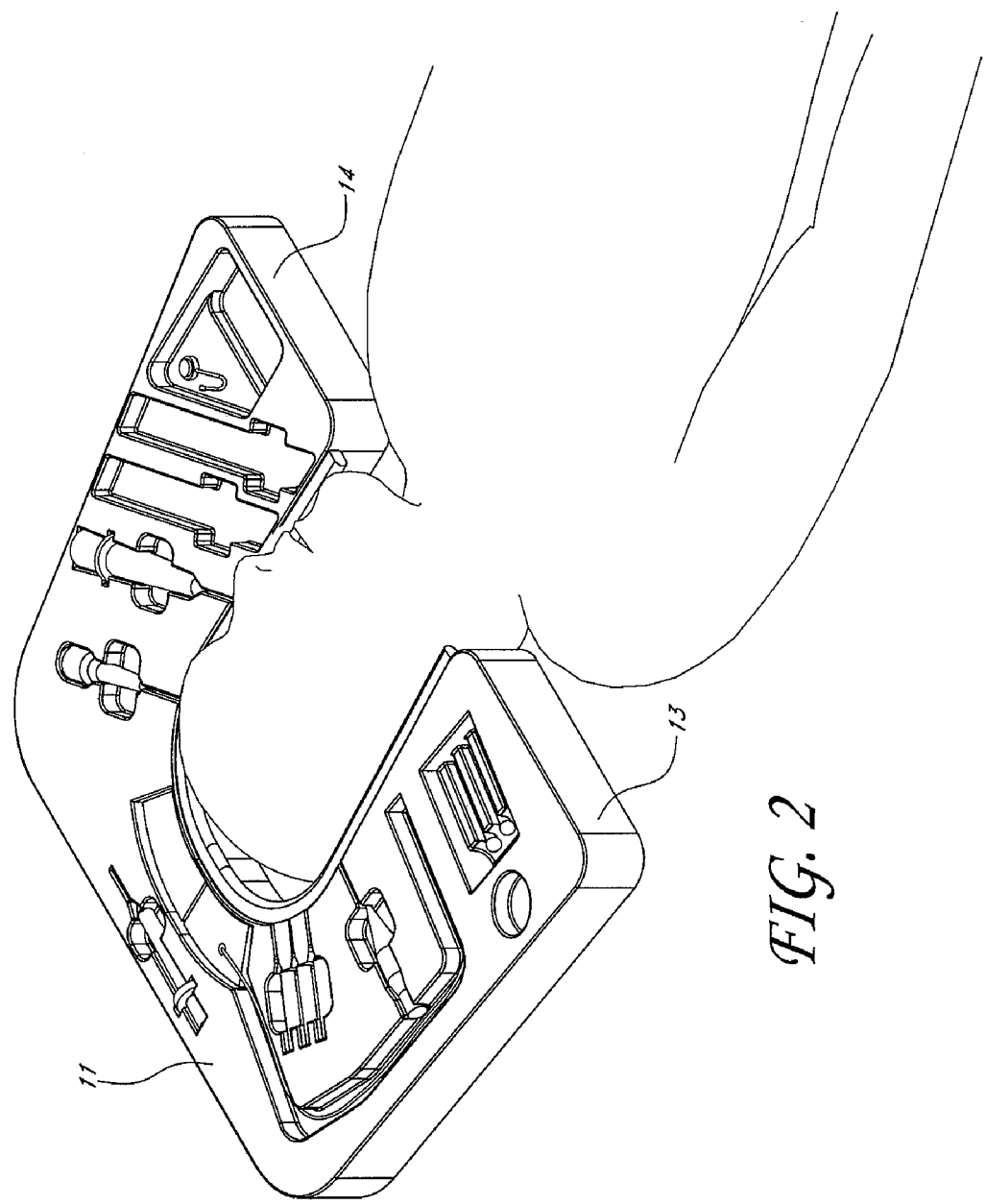
FIG. 2 illustrates an exemplary positioning of a surgical pack between a surgeon and a patient according to an embodiment of the present invention.

FIG. 2 illustrates an exemplary positioning of the tray 11 about the head of a patient according to one embodiment of the invention. According to the illustrated embodiments, the tray is substantially U-shaped or horseshoe-shaped, and is configured and sized to surround the periphery of the patient's head or other body part. A person of skill in the art should recognize, however, that any other geometric shape configured to accommodate a body part undergoing a surgical or diagnostic procedure is also contemplated. For example, the tray may have a semicircular configuration such that it effectively encircles or wraps around the patient's head. According to this embodiment, instrumentation may be placed to extend along radial directions with respect to the tray. According to another example, the tray may include substantially squared-off corners and edges instead of the rounded corners and edges depicted in FIG. 2.

According to the embodiment illustrated in FIG. 2, the tray 11 has two ends 13, 14 extending substantially along a first direction and spaced apart from each other along a second direction that is substantially perpendicular to the first direction to accommodate a head or other body part of a patient between the two ends 13, 14, with provisions for mounting a sterile barrier. The sterile barrier may include, for example, a Plexiglas plate, and may be mounted on either to side of the surgical tray or both sides of the surgical tray. A non-sterile nurse may handle one or more of the instrumentations within the sterile barrier by using rubber gloves, that part of the sterile barrier, or the like.

Figure 4:
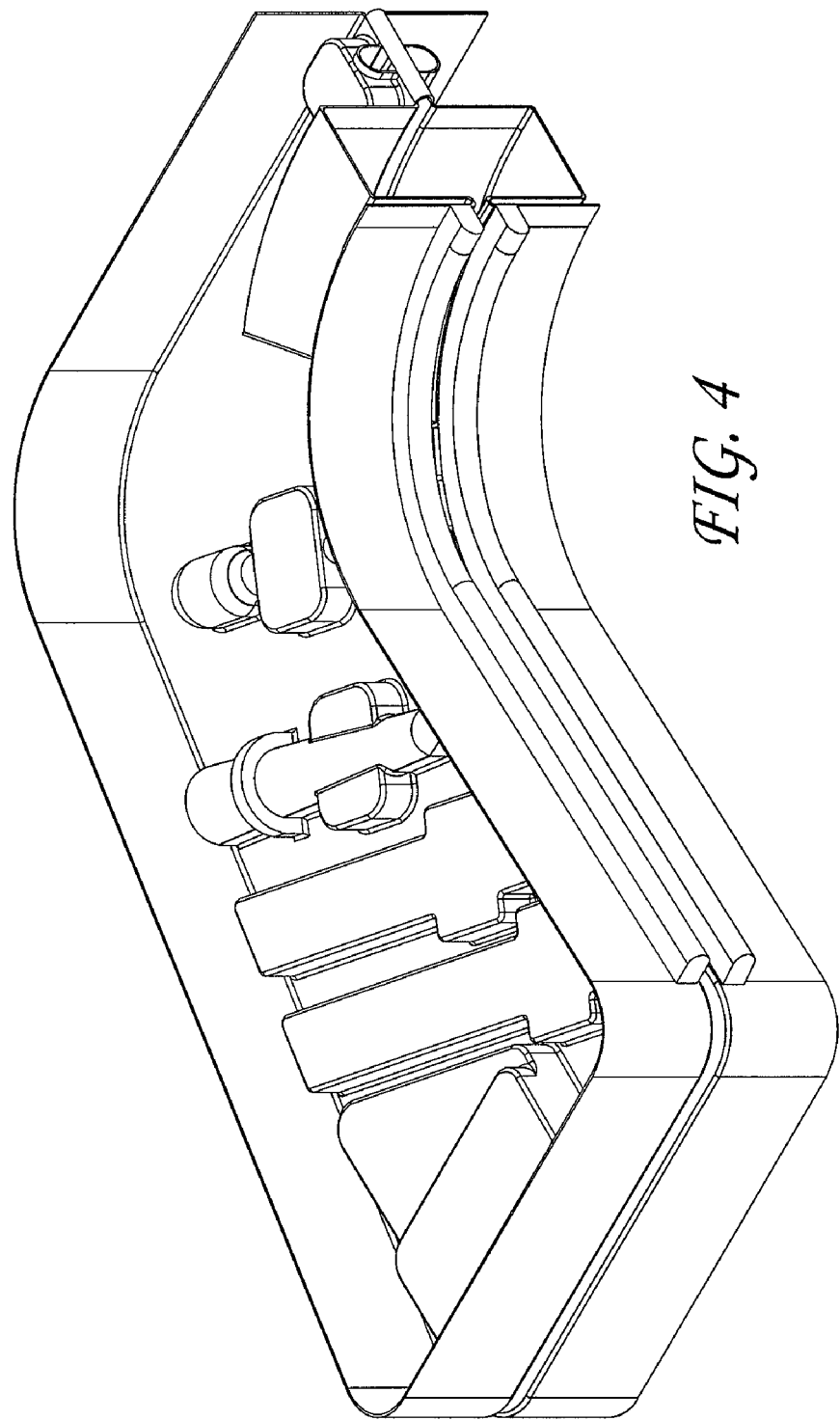
FIG. 4 illustrates a perspective view of the a surgical pack folded in half according to one embodiment of the invention.

According to one embodiment of the invention, in order to minimize the size of the packaging of the surgical pack, the tray may be configured with a hinging mechanism on the top of the tray for allowing the tray to be hinged closed as is illustrated in FIG. 4.

Figure 3:
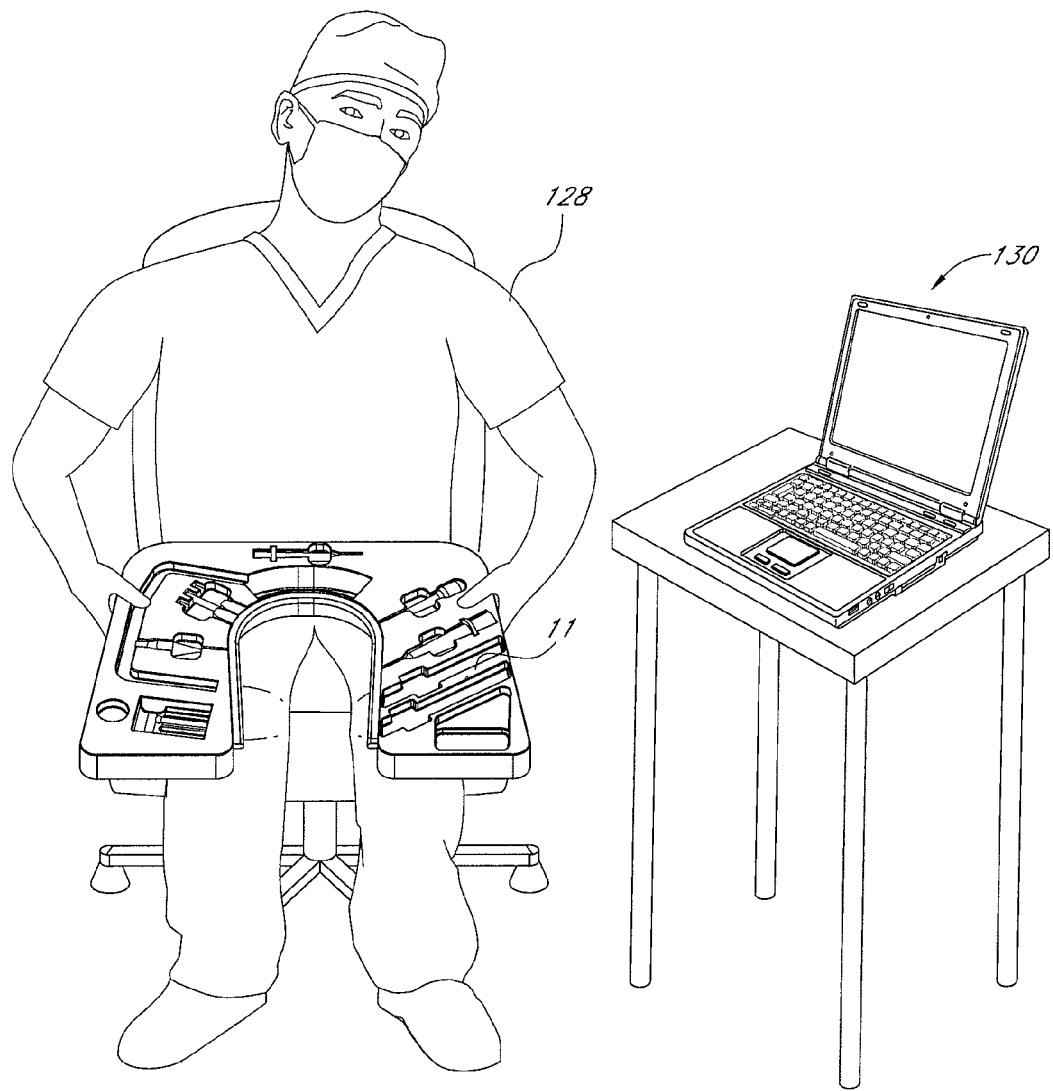
FIG. 3 illustrates an exemplary positioning of a surgical pack about the head of a patient according to an embodiment of the present invention.

FIG. 3 illustrates the position of the tray 11 with respect to a surgeon 128 utilizing the tray. The surgeon may utilize the tray to perform different types of surgical and/or consultation procedures. A console 130 may monitor and store the parameters of the instruments as described in further detail in U.S. application Ser. No. 12/107,052, entitled "Personal Surgical Center," filed on Apr. 21, 2008.

The following steps may be taken during a surgical procedure. A person of skill in the art should recognize that one or more of the steps may vary depending on the type of surgery performed:

1) The surgical pack is opened by the surgeon or a nurse to expose the surgical tray 11. The opened pack is placed in a suitable location such as, for example, on a stand or attached to a surgical platform, such that it is accessible to the surgeon. For example, as depicted in FIG. 3, the surgical tray 11 may be positioned between the surgeon and the patient.

2) According to one embodiment of the invention, all instruments needed for the surgery are retained by the tray and ready for use. The instrument locations may also be labeled. According to some embodiment, all logic, circuitry, and power to control the instruments may also be located in the tray and/or the instruments removed from the tray. Instrument locations may be labeled. The location of the instruments on the tray as well as the recesses are configured to provide easy access to those instruments by the surgeon for removal and insertion.

3) The aspiration/infusion cassette 1203 may be setup. Alternatively, if the cassette is mounted into the tray, no setup may be required.

4) The speculum/drape combination 1204 is positioned adjacent the eye or the surgical site of the eye. A second larger drape may be retrieved from the tray and positioned to cover a larger area such as, for example, the patient's head.

5) Q-tips and trocar/cannula assemblies are retrieved from the tray. The surgeon uses the Q-tips, for example, to displace the conjunctiva while inserting the cannulas with the trocar.

6) After use, the trocars are placed back in the tray so that the tips are covered or shielded to prevent accidental injury.

7) The infusion line is retrieved from the tray and attached to the cannula 1210, and the clamp is released. The appropriate infusion pressure is used to maintain intraocular pressure.

8) Triamcinolone (if required) is retrieved from the tray, injected into the eye, and the syringe is placed back on the tray. The tray safeguards all needles to prevent accidental needle-sticks.

9) The biological tissue cutter is retrieved from the tray and activated to begin cutting and aspirating for a first part of the surgical procedure. The aspiration line is primed by puncturing the top of a BSS container 1208 with the biological tissue cutter and by inserting the cutter into the sterile BSS container. The BSS container is self contained in the tray.

10) The tissue illuminator 1202 is removed from the tray, and, once removed, it turns on and is controlled at the handpiece itself.

11) The biological tissue cutter 1201 and tissue illuminator 1202 are inserted into the eye and the procedure begins.

12) After a first part of the surgical procedure when instruments are not in use, they are placed back in the tray, allowing the tips to be protected from contamination as well as damage.

13) Should the surgeon request assistance a sterile barrier may be attached to the surgical tray to allow a non-sterile assistant to assist the surgeon in the sterile field. The non-sterile assistant wears sterile protection (e.g. gloves) to reach into the sterile field.

14) When the procedure is complete, each instrument is placed in its corresponding position in the tray. The drape and speculum are removed from the patient. The tray is placed in the appropriate platform or returned to the manufacturer (e.g., a pre-packaged return container) for recycling and/or refurbishment purposes.

As described above, embodiments of the present invention facilitate convenient and efficient setup. All (or substantially all) disposable instrumentation required for a procedure, including the surgical tray, are positioned in the surgical pack. Once the pack is opened, the instrumentation can be readily retrieved from the tray by the surgeon. Once the surgeon is finished with a procedure, all instruments may be returned to the tray for disposal. It may then be recycled, sent back to the factory, or discarded.

A person skilled in the art should recognize, therefore, that there are several features to surgical packs described in accordance with the above embodiments.

1) Low cost: The tray-based surgical pack has low or at least comparable costs relative to existing surgical packs.

2) Efficient setup and teardown: As described above, embodiments of the present invention effectively provide, upon opening, a surgical tray on which instrumentation is arranged for retrieval and use by a surgeon. As such, time that would have been spent in transferring instrumentation from the pack to a separate tray or table is saved. Furthermore, upon the completion of a procedure, the surgical tray and its instruments can be placed in a separate container and sent back to the factory for recycling, refurbishment, or disposal.

3) Fewer assisting personnel: Because the transfer of instrumentation to a separate tray or table is not required, the assistance of a scrub nurse or similar assistant is not required. In addition, labeling of instrument placement as described in accordance with embodiments of the present invention assist a surgeon in independently locating and retrieving instrumentation during a procedure.

4) Adaptability for use in surgeon's offices and surgical centers: Because the surgical pack facilitates efficient setup and requires a lower degree of assistance from other surgical personnel, the surgical pack may be used in environments other than the conventional operating room.

5) Upgradeability: Surgical packs may readily be customized to suit the needs of a particular surgeon or procedure, e.g., to include or not to include certain instruments and/or components, and to position certain instruments on the tray closer or further away from a working position of the surgeon.

It will be apparent to those skilled in the art that various modifications and variations may be made in the surgical pack of the present invention without departing from the scope or spirit of the invention. For example, although the above embodiments are directed to performing ophthalmic surgeries, a person of skill in the art should recognize that the tray of the above embodiments may also be used for diagnostic procedures of the eye or any other body part. Thus, it is intended that the present invention cover the modifications and variations of this invention provided they come within the scope of the appended claims and their equivalents.

What is claimed is:

1. A surgical apparatus for use by a surgeon during an ophthalmic surgical procedure comprising:
    a tray having a plurality of recesses located on an upper side of the tray, the tray comprising an opening extending entirely through the tray from the upper side of the tray to a lower side of the tray, the opening having a U-shaped configuration, the opening sized and configured to surround a head of a human patient undergoing the ophthalmic surgical procedure in a manner such that the tray can be moved without disturbing or moving the head of the human patient;
    a plurality of surgical instruments, each of the surgical instruments being removably positioned in a corresponding one of the recesses; and
    a cover removably affixed to the tray at the upper side of the tray for covering at least the upper side of the tray and the surgical instruments, the cover being adapted to preserve the sterility of the upper side at least until the cover is removed.

2. The surgical apparatus of claim 1, wherein the tray is configured to sit on a surgical stand to the side of or on top of the human patient.

3. The surgical apparatus of claim 1, wherein the tray comprises a processing unit configured to control operation of at least one of the plurality of surgical instruments.

4. The surgical apparatus of claim 1, wherein at least one of the surgical instruments has a substantially sharp end, and wherein the one of the recesses corresponding to the at least one of the surgical instruments comprises a covering for substantially shielding the substantially sharp end.

5. The surgical apparatus of claim 1, wherein at least one of the surgical instruments has a substantially sharp end, and wherein a portion of the one of the recesses corresponding to the at least one of the surgical instruments is configured to have a shape substantially conforming to a shape of the substantially sharp end.

6. The surgical apparatus of claim 1, wherein at least one of the surgical instruments has a substantially sharp end and a handle portion, wherein the one of the recesses corresponding to the at least one of the surgical instruments has a depth configured to contain the substantially sharp end deeper in the recess than the handle portion.

7. The surgical apparatus of claim 1, wherein the tray has identifiers located in relation to the recesses, the identifiers corresponding to the surgical instruments positioned in the recesses.

8. The surgical apparatus of claim 7, wherein at least one of the identifiers includes tactile identifiers.

9. The surgical apparatus of claim 7, wherein at least one of the identifiers includes a light emitting diode (LED) display.

10. The surgical apparatus of claim 7, wherein at least one of the identifiers includes a colored code.

11. The surgical apparatus of claim 1, wherein the tray accommodates a substantially sterile barrier accessible by a substantially non-sterile user wearing substantially sterile protection for providing assistance during the ophthalmic surgical procedure.

12. The surgical apparatus of claim 1, wherein the tray comprises a power source.

13. The surgical apparatus of claim 1, further comprising a drape and a drape attachment mechanism to which the drape is removably attachable, wherein the drape is configured to be positioned adjacent to a surgical site of an eye of the human patient, and wherein the drape attachment mechanism is positioned adjacent the opening in the tray.

14. The surgical apparatus of claim 13, wherein the drape attachment mechanism comprises a ridge positioned adjacent the opening in the tray.

15. The surgical apparatus of claim 1, wherein the plurality of recesses includes a first recess on the upper side of the tray, the first recess configured to receive a balanced salt solution container.

16. A surgical apparatus comprising:
    a tray having a plurality of recesses located on an upper side of the tray the tray comprising an opening extending entirely through the tray from the upper side of the tray to a lower side of the tray, the opening having a U-shaped configuration, the opening sized and configured to surround a head of a human patient undergoing an ophthalmic surgical procedure in a manner such that the tray can be moved without disturbing or moving the head of the human patient;
    a biological tissue cutter removably positioned in a corresponding one of the recesses, thereby positioning the biological tissue cutter in close proximity to an eye of the human patient during the ophthalmic surgical procedure;
    a cover for holding the biological tissue cutter in a substantially sterile condition.

17. The surgical apparatus of claim 16, further comprising a tissue illuminator removably positioned in a second corresponding one of the recesses.

18. The surgical apparatus of claim 16, wherein the cover is removable.

19. The surgical apparatus of claim 16, further comprising a drape and a drape attachment mechanism to which the drape is removably attachable, wherein the drape is configured to be positioned adjacent to a surgical site of the eye of the human patient, and wherein the drape attachment mechanism is positioned adjacent the opening in the tray.

20. The surgical apparatus of claim 19, wherein the drape attachment mechanism comprises a ridge positioned adjacent the opening in the tray.

21. The surgical apparatus of claim 16, wherein the plurality of recesses includes a first recess on the upper side of the tray, the first recess configured to receive a balanced salt solution container.

22. A method for providing improved access to instrumentation during an ophthalmic surgical procedure, the method comprising:
   providing a surgical pack including:
      a tray having a plurality of recesses, the tray comprising an opening extending entirely through the platform from an upper side of the tray to a lower side of the tray, the opening having a U-shaped configuration, the opening sized and configured to surround a head of a human patient undergoing the ophthalmic surgical procedure in a manner such that the tray can be moved without disturbing or moving the head of the human patient;
      a plurality of surgical instruments, each of the surgical instruments being removably positioned in a corresponding one of the recesses, the corresponding one of the recesses having a shape substantially conforming to the shape of the surgical instrument being received; and
      a cover attached to the upper side of the tray for holding the plurality of surgical instruments in a substantially sterile condition;
   removing the cover from the tray;
   placing the tray such that the tray effectively surrounds the head of the human patient, thereby allowing the surgical instruments to be in close proximity to an eye of the human patient to be accessed during the ophthalmic surgical procedure;
   removing at least one of the surgical instruments from the corresponding recess for a first part of the ophthalmic surgical procedure; and
   returning the at least one of the surgical instruments to the corresponding recess after the first part of the ophthalmic surgical procedure.

23. The method of claim 22, wherein removing at least one of the surgical instruments from the corresponding recess for a first part of the ophthalmic surgical procedure comprises removing a biological tissue cutter.

24. The method of claim 22, wherein removing at least one of the surgical instruments from the corresponding recess for a first part of the ophthalmic surgical procedure comprises removing a tissue illuminator.

25. The method of claim 22, further comprises positioning a drape adjacent to a surgical site of the eye of the human patient, wherein the drape is configured to be removably attachable to a drape attachment mechanism, and wherein the drape attachment mechanism is positioned adjacent the opening in the tray.

26. The method of claim 25, wherein the drape attachment mechanism comprises a ridge positioned adjacent the opening in the tray.

27. The method of claim 22, wherein the plurality of recesses includes a first recess on the upper side of the tray, the first recess configured to receive a balanced salt solution container, and further comprises positioning the balanced salt solution container within the first recess.

28. A surgical apparatus for use by a surgeon during an ophthalmic surgical procedure comprising:
   a tray having a plurality of recesses located on an upper side of the tray, the tray comprising an opening extending entirely through the tray from the upper side of the tray to a lower side of the tray, the opening having a U-shaped configuration, the opening sized and configured to surround a head of a human patient undergoing the ophthalmic surgical procedure in a manner such that the tray can be moved without disturbing or moving the head of the human patient; and
   a plurality of surgical instruments, each of the surgical instruments being removably positioned in a corresponding one of the recesses of the tray;
   wherein the tray comprises a covering configured to preserve sterility.

29. The surgical apparatus of claim 28, further comprising a sterile barrier mounted to the tray.

30. The surgical apparatus of claim 28, wherein the tray comprises a drape configured to cover at least a portion of the head of the human patient, the drape configured to be removably coupled to an attachment site on the tray, wherein the attachment site comprises an attachment mechanism that is positioned around the opening of the tray.

31. The surgical apparatus of claim 28, further comprising a drape and a drape attachment mechanism to which the drape is removably attachable, wherein the drape is configured to be positioned adjacent to a surgical site of an eye of the human patient, and wherein the drape attachment mechanism is positioned adjacent the opening in the tray.

32. The surgical apparatus of claim 31, wherein the drape attachment mechanism comprises a ridge positioned adjacent the opening in the tray.

33. The surgical apparatus of claim 28, wherein the plurality of recesses includes a first recess on the upper side of the tray, the first recess configured to receive a balanced salt solution container.

34. A surgical apparatus for use by a surgeon during an ophthalmic surgical procedure comprising:
   a tray having a plurality of recesses located on an upper side of the tray, the tray comprising an opening extending entirely through the tray from the upper side of the tray to a lower side of the tray, the opening sized and configured to be positioned adjacent to a head of a patient undergoing the ophthalmic surgical procedure in a manner such that the tray can be moved without disturbing or moving the head of the patient, the plurality of recesses comprising a first recess on the upper side of the tray, the first recess configured to receive a balanced salt solution container;
   a plurality of surgical instruments, each of the surgical instruments being removably positioned in a corresponding one of the recesses;
   a cover removably affixed to the tray at the upper side of the tray for covering at least the upper side of the tray and the surgical instruments, the cover being adapted to preserve the sterility of the upper side at least until the cover is removed; and an illuminator disposed in relation to the first recess so to illuminate the first recess.

35. The apparatus of claim 34 for use by a surgeon during an ophthalmic surgical procedure, wherein the opening comprises a U-shaped configuration.

36. The apparatus of claim 34 for use by a surgeon during an ophthalmic surgical procedure, wherein the illuminator is a light emitting diode.

37. The apparatus of claim 34 for use by a surgeon during an ophthalmic surgical procedure, wherein the tray is configured to be positioned on a surgical stand to the side of or on top of the patient.

38. The apparatus of claim 34 for use by a surgeon during an ophthalmic surgical procedure, wherein the tray comprises a processing unit configured to control operation of at least one of the plurality of surgical instruments.

39. The apparatus of claim 34 for use by a surgeon during an ophthalmic surgical procedure, wherein at least one of the surgical instruments has a substantially sharp end, and wherein the one of the recesses corresponding to the at least one of the surgical instruments comprises a covering for substantially shielding the substantially sharp end.

40. The apparatus of claim 34 for use by a surgeon during an ophthalmic surgical procedure, wherein at least one of the surgical instruments has a substantially sharp end, and wherein a portion of the one of the recesses corresponding to the at least one of the surgical instruments is configured to have a shape substantially conforming to a shape of the substantially sharp end.

41. The apparatus of claim 34 for use by a surgeon during an ophthalmic surgical procedure, wherein at least one of the surgical instruments has a substantially sharp end and a handle portion, wherein the one of the recesses corresponding to the at least one of the surgical instruments has a depth configured to contain the substantially sharp end deeper in the recess than the handle portion.

42. The apparatus of claim 34 for use by a surgeon during an ophthalmic surgical procedure, wherein the tray has identifiers located in relation to the recesses, the identifiers corresponding to the surgical instruments positioned in the recesses.

43. The apparatus of claim 42 for use by a surgeon during an ophthalmic surgical procedure, wherein at least one of the identifiers includes tactile identifiers.

44. The apparatus of claim 42 for use by a surgeon during an ophthalmic surgical procedure, at least one of the identifiers includes a light emitting diode (LED) display.

45. The apparatus of claim 42 for use by a surgeon during an ophthalmic surgical procedure, wherein at least one of the identifiers includes a colored code.

46. The apparatus of claim 34 for use by a surgeon during an ophthalmic surgical procedure, wherein the tray accommodates a substantially sterile barrier accessible by a substantially non-sterile user wearing substantially sterile protection for providing assistance during the ophthalmic surgical procedure.

47. The apparatus of claim 34 for use by a surgeon during an ophthalmic surgical procedure, wherein the tray comprises a covering configured to preserve sterility.

48. The apparatus of claim 34 for use by a surgeon during an ophthalmic surgical procedure, further comprising a sterile barrier mounted to the tray.

49. The apparatus of claim 34 for use by a surgeon during an ophthalmic surgical procedure, wherein the tray comprises a drape configured to cover at least a portion of the head of the patient, the drape configured to be removably coupled to an attachment site on the tray, wherein the attachment site comprises an attachment mechanism that is positioned around the opening of the tray.

50. The apparatus of claim 34 for use by a surgeon during an ophthalmic surgical procedure, further comprising a drape and a drape attachment mechanism to which the drape is removably attachable, wherein the drape is configured to be positioned adjacent to a surgical site of an eye of the patient, and wherein the drape attachment mechanism is positioned adjacent the opening in the tray.

51. The apparatus of claim 50 for use by a surgeon during an ophthalmic surgical procedure, wherein the drape attachment mechanism comprises a ridge positioned adjacent the opening in the tray.

* * * * *

UNITED STATES PATENT AND TRADEMARK OFFICE
CERTIFICATE OF CORRECTION

| | | |
|---|---|---|
| PATENT NO. | : 8,177,064 B2 | Page 1 of 1 |
| APPLICATION NO. | : 12/106962 | |
| DATED | : May 15, 2012 | |
| INVENTOR(S) | : Matthew McCormick et al. | |

It is certified that error appears in the above-identified patent and that said Letters Patent is hereby corrected as shown below:

Page 2, line 22, Under Other Publications, please change 12/107.052 to --12/107,052--.

Column 1, line 46, change "cuffing" to --cutting--.

Column 3, line 42, change "the a" to --a--.

Column 4, line 16, change "112b" to --122b--.

Column 4, line 28, change "devices" to --devices.--.

Column 4, line 44, change "Triameinolone" to --Triamcinolone.--.

Column 5, line 47, change "foe" to --for.--.

Column 5, line 51, change "112b" to --122b--.

Column 7, line 47, after "either", delete "to".

Signed and Sealed this
Eighteenth Day of September, 2012

David J. Kappos
*Director of the United States Patent and Trademark Office*